United States Patent

Schlecker et al.

Patent Number: 4,618,622
Date of Patent: Oct. 21, 1986

[54] SULFONATES OF HYDROXYCOUMARINS

[75] Inventors: Rainer Schlecker, Bissersheim; Peter Schmidt, Weisenheim; Peter C. Thieme, Wachenheim; Dieter Lenke, Ludwigshafen; Hans-Juergen Teschendorf, Dudenhofen; Martin Traut, Heidelberg; Claus D. Mueller, Viernheim; Hans P. Hofmann, Limbergerhof; Horst Kreiskott, Wachenheim, all of Fed. Rep. of Germany

[73] Assignee: BASF Aktiengesellschaft, Ludwigshafen, Fed. Rep. of Germany

[21] Appl. No.: 552,787

[22] Filed: Nov. 17, 1983

[30] Foreign Application Priority Data

Nov. 23, 1982 [DE] Fed. Rep. of Germany ....... 3243158

[51] Int. Cl.⁴ .................. C07D 311/08; A61K 31/37
[52] U.S. Cl. .................. 514/457; 549/280; 549/287; 549/289
[58] Field of Search ............ 549/289, 280, 287; 514/457

[56] References Cited

PUBLICATIONS

Dragota et al., CA, 86: 121104w.
Narayanan et al., CA, 90: 151932q.
Izvest. Akad. Nauk Armyan. S.S.R., Ser. khim. Nauk, 10, (1957), 353 (C.A., 52, 12854f).

Primary Examiner—Jane T. Fan
Attorney, Agent, or Firm—Keil & Weinkauf

[57] ABSTRACT

Sulfonates of hydroxycoumarins of the formula I

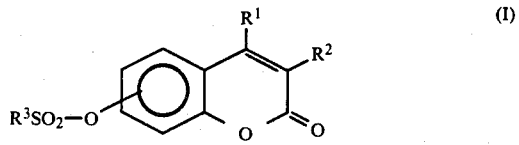

where $R^1$ and $R^2$ are identical or different and are each hydrogen, halogen or alkyl of 1 to 5 carbon atoms which can be substituted by $-NR^4R^5$, $-OR^4$ or $-OC(O)R^4$, where $R^4$ and $R^5$ are identical or different and are each hydrogen or alkyl of 1 to 4 carbon atoms, or $R^1$ and $R^2$ are each a carboxylic acid group $-OC(O)R^4$ or a carboxamido radical, with the proviso that $R^1$ is not methyl when $R^2$ is hydrogen, or $R^1$ and $R^2$ together form a $-(CH_2)_n-$ chain where n is 3-5, and $R^3$ is a straight-chain or branched alkyl radical of 1 to 8 carbon atoms or cycloalkyl of 3 to 8 carbon atoms, each of which can be substituted by halogen, $-OR^4$, $-NR^4R^5$, $-CN$ or phenyl, or $R^3$ is a straight-chain or branched alkenyl radical of 3 to 8 carbon atoms, an amino group $-NR^4R^5$, or phenyl or naphthyl, each of which is unsubstituted or monosubstituted or polysubstituted by $-OR^4$, $-NR^4R^5$, $-NO_2$, halogen, $-SR^4$, $-S(O)R^4$, $-OS(O)R^4$, $-SCF_3$, $-OS(O)CF_3$, $-CN$, $-C(O)R^4$, $-OC(O)R^4$, $-NHC(O)R^4$, $-CF_3$, $C_1-C_4$-alkyl or a combination of these substituents, a process for their preparation, drugs containing these compounds, and compounds of the formula I, in which $R^1$ is methyl and $R^2$ is hydrogen, for use as drugs.

8 Claims, No Drawings

SULFONATES OF HYDROXYCOUMARINS

The present invention relates to novel sulfonates of hydroxycoumarins, a process for their preparation and pharmaceutical formulations which contain these compounds as active compounds and are useful drugs in the treatment of psychological disturbances, in particular depression, and of allergies.

Izvest. Akad. Nauk Armyan. S.S.R., Ser. khim. Nauk 10 (1957), 353 (C.A. 52, 12854f) describes a number of sulfonates of 7-hydroxy-4-methylcoumarins which have an insecticidal action, but no information is given concerning the antidepressant activity of these compounds.

We have found that compounds of the general formula I

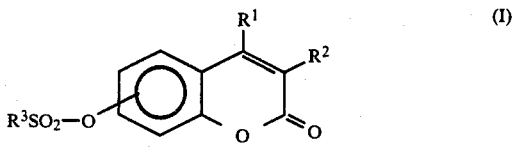

where $R^1$ and $R^2$ are identical or different and are each hydrogen, halogen, preferably chlorine, or alkyl of 1 to 5 carbon atoms which can be substituted by $-NR^4R^5$, $-OR^4$ or $-OC(O)R^4$, where $R^4$ and $R^5$ are identical or different and are each hydrogen or alkyl of 1 to 4 carbon atoms, or $R^1$ and $R^2$ are each a carboxylic acid group $-OC(O)R^4$ or a carboxamido radical, with the proviso that $R^1$ is not methyl when $R^2$ is hydrogen, or $R^1$ and $R^2$ together form a $-(CH_2)_n-$ chain where n is 3–5, and $R^3$ is a straight-chain or branched alkyl radical of 1 to 8 carbon atoms or cycloalkyl of 3 to 8 carbon atoms, each of which can be substituted by halogen, $-OR^4$, $-NR^4R^5$, $-CN$ or phenyl, or $R^3$ is a straight-chain or branched alkenyl radical of 3 to 8 carbon atoms, an amino group $-NR^4R^5$, or phenyl or naphthyl, each of which is unsubstituted or substituted by $-OR^4$, $-NR^4R^5$, $-NO_2$, halogen, $-SR^4$, $-S(O)R^4$, $-OS(O)R^4$, $-OS(O)CF_3$, $-SCF_3$, $-OS(O)CF_3$, $-CN$, $-C(O)R^4$, $-OC(O)R^4$, $-NHC(O)R^4$, $-CF_3$, $C_1-C_4$-alkyl or a combination of these substituents, have useful pharmacological properties.

The novel compounds of the formula I can be prepared by a process in which a hydroxycoumarin of the formula II

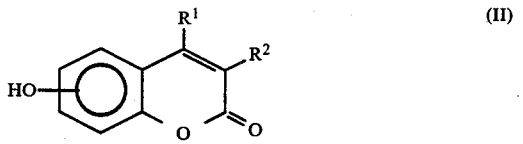

where $R^1$ and $R^2$ have the above meanings, is reacted in a conventional manner with a sulfonic acid derivative of the formula III

where $R^3$ has the meanings given for formula I and X is a nucleofugic leaving group, eg. chlorine, bromine or $R^3SO_2O$. The reaction can be carried out as described in, for example, Houben-Weyl, Georg Thieme-Verl., Stuttgart 1966, Vol. 9, pages 671–674, by heating the two components, preferably in the presence of an inert solvent, such as benzene, toluene, methylene chloride, acetone, ethanol, dimethylformamide or water. The acid liberated is generally captured by adding a base, such as an alkali metal or alkaline earth metal hydroxide or carbonate or an amine, such as dimethylaniline or pyridine. The base, used in excess, can also serve as the solvent. Instead of the hydroxycoumarins of the formula II, it is also possible to react their alkali metal salts with the sulfonic acid derivatives III, preferably under anhydrous conditions in an aprotic solvent, eg. ether, tetrahydrofuran, dimethylformamide (DMF) or dimethyl sulfoxide (DMSO). Suitable bases in these cases are alkali metal hydrides or alcoholates.

Furthermore, compounds of the formula I where $R^3$ is a substituted aromatic radical can be prepared by a conventional process, by introducing a new substituent or converting a substituent which is already present to $R^3$. This can be done using a conventional method of the chemistry of aromatics. For example, hydroxycoumarin alkylsulfonylbenzenesulfonates can be readily obtained by oxidation of the corresponding hydroxycoumarin alkylthiobenzenesulfonates with an oxidizing agent, such as hydrogen peroxide or a peracid.

The hydroxycoumarins II can be prepared by a conventional method, as described by, for example, Elderfield R. C. in Heterocyclic Compounds, published by John Wiley, New York 1951, Vol. 2, page 174 et seq., for example by condensation of a dihydroxybenzene with a β-ketocarboxylate of the formula $$R^1-CO-CHR^2-CO_2C_2H_5$$

in the presence of a condensing agent, such as sulfuric acid, phosphorus pentoxide or aluminum chloride.

The sulfonic acid derivatives of the formula III are predominantly available commercially or known from the literature, and can be prepared by conventional processes, as summarized in Houben-Weyl, Vol. 9, pages 389–398 and pages 547–599.

Examples of novel pharmaceutical active compounds which are obtained by the stated processes are methane-, ethane-, propane-, isopropane-, butane-, isobutane-, sec.-butane-, tert.-butane-, pentane-, 1-methylbutane-, 2-methylbutane-, isopentane-, 1,1-dimethylpropane-, 2,2-dimethylpropane-, hexane-, heptane-, octane-, 2-chloroethane-, 3-chloropropane-, 3-chlorobutane-, trifluoromethane-, 2,2,2-trifluoroethane-, trichloromethane-, 2-methoxyethane-, 3-methoxypropane-, 3-methoxybutane-, 4-methoxybutane-, 2-ethoxyethane-, 2-dimethylaminoethane-, 3-dimethylaminopropane-, 4-dimethylaminobutane-, 3-dimethylaminobutane-, 5-dimethylaminopentane-, 3-methylaminopropane-, cyclopropane-, 1-methylcyclopropane-, 2-methylcyclopropane-, 2,2-dimethylcyclopropane-, 1,2,2-trimethylcyclopropane-, 2,2,3-trimethylcyclopropane-, cyclobutane-, 1-methylcyclobutane-, 2-methylcyclobutane-, 3-methylcyclobutane-, 1-propylcyclobutane-, 1-butylcyclobutane-, cyclopentane-, 1-methylcyclopentane-, 2,5-dimethylcyclopentane-, cyclohexane-, 1-methylcyclohexane-, cycloheptane-, cyclooctane-, ethene-, prop-1-ene-, prop-2-ene-, isopropene-, 1-methylprop-1-ene-, 2-methylprop-1-ene-, 1-methylprop-2-ene-, but-1-ene-, but-2-ene-, but-3-ene-, 1,2-dimethylprop-1-ene-, 1-ethylprop-1-ene-, 2-methylbut-1-ene-, 3-methylbut-1-ene-, 1-methylbut-2-ene-, pent-1-ene-, pent-2-ene-, pent-3-ene-, pent-4-ene-, 1-ethylbut-1-ene-, 2-ethylbut-1-ene, 2-methylpent-1-ene-, 3-methylpent-1-ene-, 3-methylpent-2-ene-, hex-3-ene-, hex-5-ene-, 2-ethyl-1-methylbut-1-ene-, hept-1-ene-, hept-6-ene-, oct-1-ene-, oct-7-ene-, 2-toluene-, 3-toluene-, 4-toluene-, 3-ethylbenzene-, 4-ethylbenzene-, 4-propylbenzene-, 2,3-dimethylbenzene-, 2,4-dimethylbenzene-, 2,5-dimethylbenzene-, 2,6-dimethylbenzene-, 3,4-dimethylbenzene-, 3,5-dimethylbenzene-, 2,4,6-trimethylbenzene-, 2-methoxybenzene-, 3-methoxybenzene-, 4-methoxybenzene-, 2-ethoxybenzene-, 4-ethoxybenzene-, 2,3-dimethoxybenzene-, 2,4-dimethoxybenzene-, 2,6-dimethoxybenzene-, 3,4-dimethoxybenzene-, 2,4,6-trimethoxybenzene-, 2-chlorobenzene-, 3-chlorobenzene-, 4-chlorobenzene-, 2-bromobenzene-, 3-bromobenzene-, 4-bromobenzene-, 2-fluorobenzene-, 3-fluorobenzene-, 4-fluorobenzene-, 2-nitrobenzene-, 3-nitrobenzene-, 4-nitrobenzene-, 2-cyanobenzene-, 3-cyanobenzene-, 4-cyanobenzene-, 2-methylthiobenzene-, 3-methylthiobenzene-, 4-methylthiobenzene-, 2-ethylthiobenzene-, 3-ethylthiobenzene-, 4-ethylthiobenzene-, 2-methylsulfonylbenzene-, 3-methylsulfonylbenzene-, 4-methylsulfonylbenzene-, 2-methylsulfinylbenzene-, 4-methylsulfinylbenzene-, 2-acetylbenzene-, 3-acetylbenzene-, 4 acetylbenzene-, 3-acetylaminobenzene-, 4-acetylaminobenzene-, 2-carbomethoxybenzene-, 3-carbomethoxybenzene-, 4-carbomethoxybenzene-, 2-aminobenzene-, 3-aminobenzene-, 4-aminobenzene-, 3-methylaminobenzene-, 4-methylaminobenzene-, 3-dimethylaminobenzene-, 4-dimethylaminobenzene-, 2,3-dichlorobenzene-, 2,4-dichlorobenzene-, 2,5-dichlorobenzene-, 2,6-dichlorobenzene-, 3,4-dichlorobenzene-, 3,5-dichlorobenzene-, 2,4-difluorobenzene-, 2,5-difluorobenzene-, 2,6-difluorobenzene-, 2-chloro-6-fluorobenzene-, 3-chloro-4-fluorobenzene-, 2-(trifluoromethyl)-benzene-, 3-(trifluoromethyl)-benzene-, 4-(trifluoromethyl)-benzene-, 2-chloro-4-methylbenzene-, 2-chloro-5-methylbenzene-, 4-chloro-2-methylbenzene-, 4-chloro-3-methylbenzene-, 3-chloro-4-methoxybenzene-, 4-chloro-2-methoxybenzene-, 3-fluoro-4-methylbenzene-, 4-fluoro-3-methylbenzene-, 4-chloro-2-(trifluoromethyl)-benzene-, 4-chloro-3-(trifluoromethyl)-benzene-, 4-fluoro-3-(trifluoromethyl)-benzene-, 4-chloro-3-nitrobenzene-, 3-chloro-4-nitrobenzene-, 3-fluoro-4-nitrobenzene-, 4-nitro-3-(trifluoromethyl)-benzene-, naphthalene-1- and naphthalene-2-sulfonates of 5-hydroxycoumarin, 6-hydroxycoumarin, 7-hydroxycoumarin, 8-hydroxycoumarin, 5-hydroxy-3-methylcoumarin, 6-hydroxy-3-methylcoumarin, 7-hydroxy-3-methylcoumarin, 8-hydroxy-3-methylcoumarin, 5-hydroxy-4-methylcoumarin, 6-hydroxy-4-methylcoumarin, 7-hydroxy-4-methylcoumarin, 8-hydroxy-4-methylcoumarin, 3,4-dimethyl-5-hydroxycoumarin, 3,4-dimethyl-6-hydroxycoumarin, 3,4-dimethyl-7-hydroxycoumarin, 3,4-dimethyl-8-hydroxycoumarin, 4-ethyl-5-hydroxycoumarin, 4-ethyl-6-hydroxycoumarin, 4-ethyl-7-hydroxycoumarin, 4-ethyl-8-hydroxycoumarin, 3-ethyl-5-hydroxycoumarin, 3-ethyl-6-hydroxycoumarin, 3-ethyl-7-hydroxycoumarin, 3-ethyl-8-hydroxycoumarin, 4-ethyl-5-hydroxy-3-methylcoumarin, 4-ethyl-6-hydroxy-3-methylcoumarin, 4-ethyl-7-hydroxy-3-methylcoumarin, 4-ethyl-8-hydroxy-3-methylcoumarin, 3-ethyl-5-hydroxy-4-methylcoumarin, 3-ethyl-6-hydroxy-4-methylcoumarin, 3-ethyl-7-hydroxy-4-methylcoumarin, 3-ethyl-8-hydroxy-4-methylcoumarin, 3,4-diethyl-5-hydroxycoumarin, 3,4-diethyl-6-hydroxycoumarin, 3,4-diethyl-7-hydroxycoumarin, 3,4-diethyl-8-hydroxycoumarin, 5-hydroxy-4-methyl-3-propylcoumarin, 6-hydroxy-4-methyl-3-propylcoumarin, 7-hydroxy-4-methyl-3-propylcoumarin, 8-hydroxy-4-methyl-3-propylcoumarin, 4-ethyl-5-hydroxy-3-propylcoumarin, 4-ethyl-6-hydroxy-3-propylcoumarin, 4-ethyl-7-hydroxy-3-propylcoumarin, 4-ethyl-8-hydroxy-3-propylcoumarin, 5-hydroxy-3-methyl-4-propylcoumarin, 6-hydroxy-3-methyl-4-propylcoumarin, 7-hydroxy-3-methyl-4-propylcoumarin, 8-hydroxy-3-methyl-4-propylcoumarin, 3-ethyl-5-hydroxy-4-propylcoumarin, 3-ethyl-6-hydroxy-4-propylcoumarin, 3-ethyl-7-hydroxy-4-propylcoumarin, 3-ethyl-8-hydroxy-4-propylcoumarin, 3,4-dipropyl-5-hydroxycoumarin, 3,4-dipropyl-6-hydroxycoumarin, 3,4-dipropyl-7-hydroxycoumarin, 3,4-dipropyl-8-hydroxycoumarin, 4-butyl-5-hydroxy-3-methylcoumarin, 4-butyl-6-hydroxy-3-methylcoumarin, 4-butyl-7-hydroxy-3-methylcoumarin, 4-butyl-8-hydroxy-3-methylcoumarin, 4-butyl-3-ethyl-5-hydroxycoumarin, 4-butyl-3-ethyl-6-hydroxycoumarin, 4-butyl-3-ethyl-7-hydroxycoumarin, 4-butyl-3-ethyl-8-hydroxycoumarin, 5-hydroxy-3-methyl-4-pentylcoumarin, 6-hydroxy-3-methyl-4-pentylcoumarin, 7-hydroxy-3-methyl-4-pentylcoumarin, 8-hydroxy-3-methyl-4-pentylcoumarin, 5-hydroxy-4-methyl-3-pentylcoumarin, 6-hydroxy-4-methyl-3-pentylcoumarin, 7-hydroxy-4-methyl-3-pentylcoumarin, 8-hydroxy-4-methyl-3-pentylcoumarin, 5-hydroxy-3,4-trimethylenecoumarin, 6-hydroxy-3,4-trimethylenecoumarin, 7-hydroxy-3,4-trimethylenecoumarin, 8-hydroxy-3,4-trimethylenecoumarin, 5-hydroxy-3,4-tetramethylenecoumarin, 6-hydroxy-3,4-tetramethylenecoumarin, 7-hydroxy-3,4-tetramethylenecoumarin, 8-hydroxy-3,4-tetramethylenecoumarin, 5-hydroxy-3,4-pentamethylenecoumarin, 6-hydroxy-3,4-pentamethylenecoumarin, 7-hydroxy-3,4-pentamethylenecoumarin, 8-hydroxy-3,4-pentamethylenecoumarin, 5-hydroxy-3-methoxycarbonyl-4-methylcoumarin, 6-hydroxy-3-methoxycarbonyl-4-methylcoumarin, 7-hydroxy-3-methoxycarbonyl-4-methylcoumarin, 8-hydroxy-3-methoxycarbonyl-4-methylcoumarin, 5-hydroxy-3-methoxymethyl-4-methylcoumarin, 6-hydroxy-3-methoxymethyl-4-methylcoumarin, 7-hydroxy-3-methoxymethyl-4-methylcoumarin, 8-hydroxy-3-methoxymethyl-4-methylcoumarin, 3-(2'-dimethylaminoethyl)-5-hydroxy-4-methylcoumarin, 3-(2'-dimethylaminoethyl)-6-hydroxy-4-methylcoumarin, 3-(2'-dimethylaminoethyl)-7-hydroxy-4-methylcoumarin, 3-(2'-dimethylaminoethyl)-8-hydroxycoumarin, 3-(3'-dimethylaminopropyl)-7-hydroxy-4-methylcoumarin, 3-(3'-dimethylaminopropyl)-6-hydroxy-4-methylcoumarin, 5-hydroxy-3-chlorocoumarin, 6-hydroxy-3-chlorocoumarin, 7-hydroxy-3-chlorocoumarin, 8-hydroxy-3-chlorocoumarin, 5-hydroxy-4-chlorocoumarin, 6-hydroxy-4-chlorocoumarin, 7-hydroxy-4-chlorocoumarin, 8-hydroxy-4-chlorocoumarin, 5-hydroxy-3,4-dichlorocoumarin, 6-hydroxy-3,4-dichlorocoumarin, 7-hydroxy-3,4-dichlorocoumarin, 8-hydroxy-3,4-dichlorocoumarin, 5-hydroxy-3-chloro-4-methylcoumarin, 6-hydroxy-3-chloro-4-methylcoumarin, 7-hydroxy-3-chloro-4-methylcoumarin, 8-hydroxy-3-chloro-4-methylcoumarin, 5-hydroxy-4-chloro-3-methylcoumarin, 6-hydroxy-4-chloro-3-methylcoumarin, 7-hydroxy-4-chloro-3-methylcoumarin, 8-hydroxy-4-chloro-3-methylcoumarin, 5-hydroxy-3-fluorocoumarin, 6-hydroxy-3-fluorocoumarin, 7-hydroxy-3-fluorocoumarin, 8-hydroxy-3-fluorocoumarin, 5-hydroxy-4-fluorocoumarin, 6-hydroxy-4-fluorocoumarin, 7-hydroxy-4-fluorocoumarin, 8-hydroxy-4-fluorocoumarin, 5-hydroxy-3,4-difluorocoumarin, 6-hydroxy-3,4-difluorocoumarin, 7-hydroxy-3,4-difluorocoumarin, 8-hydroxy-3,4-difluorocoumarin, 5-hydroxy-3-fluoro-4-methylcoumarin, 6-hydroxy-3-fluoro-4-methylcoumarin, 7-hydroxy-3-fluoro-4-methylcoumarin, 8-hydroxy-3-fluoro-4-methylcoumarin, 5-hydroxy-4-fluoro-3-methylcoumarin, 6-hydroxy-4-fluoro-3-methylcoumarin, 7-hydroxy-4-fluoro-3-methylcoumarin, 8-hydroxy-4-fluoro-3-methylcoumarin, 5-hydroxy-3-bromocoumarin, 6-hydroxy-3-bromocoumarin, 7-hydroxy-3-bromocoumarin, 8-hydroxy-3-bromocoumarin, 5-hydroxy-4-bromocoumarin, 6-hydroxy-4-bromocoumarin, 7-hydroxy-4-bromocoumarin, 8-hydroxy-4-bromocoumarin, 5-hydroxy-3,4-dibromocoumarin, 6-hydroxy-3,4-dibromocoumarin, 7-hydroxy-3,4-dibromocoumarin, 8-hydroxy-3,4-dibromocoumarin, 5-hydroxy-3-chloro-4-methylcoumarin, 6-hydroxy-3-bromo-4-methylcoumarin, 7-hydroxy-3-bromo-4-methylcoumarin, 8-hydroxy-3-bromo-4-methylcoumarin, 5-hydroxy-4-bromo-3-methylcoumarin, 6-hydroxy-4-bromo-3-methylcoumarin, 7-hydroxy-4-bromo-3-methylcoumarin, 8-hydroxy-4-bromo-3-methylcoumarin.

Finally, the present invention relates to drugs which, in addition to conventional carriers and diluents, contain a compound of the formula I as an active compound.

The novel compounds possess useful pharmacological properties, and can be used in the pharmacotherapy of psychological disturbances, in particular as highly effective antidepressants. They can be administered in a conventional manner, for example orally or intravenously. The dosage depends on the age, condition and weight of the patient and on the route of administration. As a rule, the daily dose of active compound is from about 5 to 100 mg for oral administration.

The types of effects displayed by the substances according to the invention were determined by the tests below:

Antidepressant action

In male mice (Swiss strain) weighing 20–26 g, reserpine (2.15 mg/kg, administered subcutaneously) lowers the body temperature by an average of 3° C., measured 2 hours after administration and at an ambient temperature of 20°–22° C. Antidepressants inhibit this hypothermia, the inhibition being dose-dependent. The test substances are administered orally, 60 minutes before the reserpine.

The dose which inhibits the reserpine-induced hypothermia by 50%, ie. the $ED_{50}$, is determined from the linear regression between log dose (mg/kg) and relative decrease in hypothermia.

Inhibition of monoaminoxidase

Monoaminoxidase A is determined in dilute rat brain homogenate to which
1. various concentrations of the test substances and
2. $^{14}C$-tryptamine in a concentration of 0.4 μmol/liter are added. This mixture is incubated at 37° C. for 20 minutes, after which the reaction is terminated by means of aqueous 0.1N HCl, and the products are extracted with toluene scintillator (PPO+POPOP in toluene) and then determined. The blank value is determined in similar mixtures for an incubation time of t=0 minutes.

The mean inhibitory concentration ($IC_{50}$) is calculated from the inhibitory values determined, in comparison with the control, at the various inhibitor concentrations, by means of a linear regression after logit-log transformation.

The results found in the reserpine test are summarized in Table 1.

All of the 22 examples listed in the table have dose-dependent actions with $ED_{50}$ values of from 0.3 (Example 52) to 29.7 mg (Example 41). The majority of the ED values found are below 4 mg, and the substances may therefore be regarded as being highly effective.

The action mechanism for the substances was found to consist in inhibition of monoaminoxidase A; the comparative substance pargyline is also known to have this action mechanism. As a measure of the antidepressant action in the reserpine test, pargyline is found to have an $ED_{50}$ of 48 mg (cf. Table 1). Comparison of the listed examples with pargyline shows that all 22 examples are more effective than pargyline, 16 of them by a factor of more than 10.

The values obtained for the inhibition of monoaminoxidase A for all the examples are summarized in Table 2.

All examples show dose-dependent inhibitory actions against monoaminoxidase A, so that an $IC_{50}$ value can be given for each substance. These $IC_{50}$ values range from a maximum of 0.7 (Example 33) to a minimum of 0.003 (Example 10) μmol/liter. For the majority of the substances, the $IC_{50}$ values found are below 0.1 μmol/liter. All of the substances are more effective (from 3 to 666 times) than pargyline, which has an $IC_{50}$ of 2.0 μmol/liter in this test model.

On the basis of the pharmacological findings, the novel substances, in an appropriate pharmaceutical formulation, are useful for the pharmacotherapy of psychological disturbances, in particular depression.

TABLE 1

| Example No. | Antidepressant action (mouse) $ED_{50}$ mg/kg, oral administration |
|---|---|
| 1 | 1.2 |
| 2 | 5.9 |
| 4 | 4.0 |
| 9 | 6.1 |
| 11 | 2.5 |
| 14 | 1.4 |
| 18 | 3.6 |
| 22 | 1.4 |
| 23 | 3.1 |
| 24 | 3.7 |
| 26 | 1.8 |
| 30 | 9.0 |
| 38 | 1.4 |
| 39 | 1.7 |
| 40 | 8.7 |
| 41 | 29.7 |
| 42 | 19.6 |
| 43 | 1.9 |
| 52 | 0.3 |
| 55 | 1.3 |
| 56 | 3.4 |
| 57 | 1.5 |
| Pargyline | 48 |

TABLE 2

| Example No. | Monoaminoxidase inhibition $IC_{50}$ μmol/liter |
|---|---|
| 1 | 0.024 |
| 2 | 0.11 |
| 3 | 0.076 |
| 4 | 0.080 |
| 5 | 0.016 |
| 6 | 0.11 |
| 7 | 0.021 |
| 8 | 0.16 |

TABLE 2-continued

| Example No. | Monoaminoxidase inhibition IC$_{50}$ µmol/liter |
|---|---|
| 9 | 0.0050 |
| 10 | 0.0029 |
| 11 | 0.0060 |
| 12 | 0.051 |
| 13 | 0.027 |
| 14 | 0.0077 |
| 15 | 0.62 |
| 16 | 0.039 |
| 17 | 0.056 |
| 18 | 0.0080 |
| 19 | 0.0098 |
| 20 | 0.067 |
| 21 | 0.55 |
| 22 | 0.0096 |
| 23 | 0.0037 |
| 24 | 0.075 |
| 25 | 0.077 |
| 26 | 0.0073 |
| 27 | 0.034 |
| 28 | 0.29 |
| 29 | 0.11 |
| 30 | 0.0063 |
| 31 | 0.030 |
| 32 | 0.12 |
| 33 | 0.70 |
| 34 | 0.023 |
| 35 | 0.12 |
| 36 | 0.093 |
| 37 | 0.067 |
| 38 | |
| 39 | 0.0084 |
| 40 | 0.0065 |
| 41 | 0.034 |
| 42 | 0.13 |
| 43 | |
| 45 | 0.16 |
| 46 | 0.077 |
| 47 | 0.11 |
| 48 | 0.022 |
| 50 | 0.54 |
| 51 | 0.54 |
| 52 | 0.0057 |
| 53 | 0.19 |
| 54 | |
| 55 | |
| 56 | |
| 57 | |
| 58 | |
| 59 | 0.22 |
| 60 | 0.014 |
| 61 | |
| Pargyline | 2.0 |

The novel active compounds can be used in the conventional solid or liquid pharmaceutical forms for administration, such as tablets, capsules, powders, granules, coated tablets or solutions. These are prepared in a conventional manner, and to do so the active compounds can be mixed with the conventional pharmaceutical auxiliaries (mainly carriers and diluents), such as talc, gum arabic, sucrose, lactose, cereal or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. H. Sucker et al., Pharmazeutische Technologie, Thieme-Verlag, Stuttgart 1978). The formulations thus obtained normally contain from 0.1 to 93% by weight of the active compound. Preparation of starting compounds:

3,4-Dimethyl-7-hydroxycoumarin

A mixture of 58 g (0.53 mole) of resorcinol and 90 g (0.53 mole) of ethyl 2-methylacetoacetate (85%) was added dropwise to 260 g of concentrated sulfuric acid at 10° C. in the course of 3–4 hours. The mixture was stirred overnight at room temperature and then poured onto 2,000 g of ice. The precipitate was filtered off under suction and suspended in 2 liters of water. The mixture was rendered strongly alkaline by the addition of concentrated sodium hydroxide solution and was then filtered, the filtrate was acidified with concentrated HCl and the precipitate was filtered off under suction, washed with water and dried. Yield: 85.2 g (85%), mp.: 258° C.

Using the same method, for example, the following compounds were prepared:

6-Hydroxy-4-methylcoumarin, yield: 67%, mp.: 245°–247° C.

7-Hydroxy-4-methyl-3-propylcoumarin, yield: 70%, mp.: 136° C.

3-Ethyl-7-hydroxy-4-methylcoumarin, yield: 79%, mp.: 195° C.

4-Ethyl-7-hydroxy-3-methylcoumarin, yield 65%, mp.: 184° C.

4-Ethyl-7-hydroxycoumarin, yield 90%, mp.: 168° C.

6-Hydroxy-3,4-dimethylcoumarin, yield: 14%, mp.: 239° C.

7-Hydroxy-4-methylcoumarin, yield 81%, mp.: 179°–182° C.

Ethyl 7-hydroxycoumarin-3-acetate 30 g (0.36 mole) of piperidine were added to 50 g (0.36 mole) of 2,4-dihydroxybenzaldehyde and 58 g (0.36 mole) of diethyl malonate, while cooling, and the mixture was then stirred for 4 hours at room temperature. 500 ml of water were added, after which the solution was brought to pH 8 with concentrated hydrochloric acid, and the precipitate was filtered off under suction, washed with water and dried. Yield: 38 g (45%), mp.: 168°–170° C. Preparation of active compounds according to the invention:

EXAMPLE 1

7-Hydroxy-3,4-dimethylcoumarin benzenesulfonate 2.3 g of 7-hydroxy-3,4-dimethylcoumarin were dissolved in 50 ml of pyridine, and 4.7 g of benzenesulfonyl chloride were added at 20° C. The mixture was stirred overnight and then poured onto 200 g of ice, and the precipitate was filtered off under suction, washed with water, recrystallized from ethanol and dried. Yield: 3.3 g (83%), mp.: 177°–178° C.

$C_{17}H_{14}O_5S$ (330) Calculated: 61.8 C, 4.3 H, 24.2 O. Found: 62.1 C, 4.3 H, 23.9 O.

Using the same method, the following compounds were prepared:

EXAMPLE 2

7-Hydroxy-3,4-dimethylcoumarin methanesulfonate

Yield: 69%, mp.: 185° C.

$C_{12}H_{12}O_5S$ (268) Calculated: 53.7 C, 4.5 H. Found: 53.8 C, 4.3 H.

EXAMPLE 3

7-Hydroxy-3,4-dimethylcoumarin naphthalene-1'-sulfonate

Yield: 91%, mp.: 144°–146° C.

$C_{21}H_{16}O_5S$ (380) Calculated: 66.3 C, 4.2 H, 8.4 S. Found: 66.2 C, 4.3 H, 8.3 S.

EXAMPLE 4

7-Hydroxy-3,4-dimethylcoumarin naphthalene-2'-sulfonate

Yield: 68%, mp.: 135°–136° C.
$C_{21}H_{16}O_5S$ (380) Calculated: 66.3 C, 4.2 H. Found: 66.6 C, 4.5 H.

EXAMPLE 5

7-Hydroxy-3,4-dimethylcoumarin toluene-4'-sulfonate $C_{18}H_{16}O_5S$ (340) Calculated: 62.8 C, 4.7 H, 23.2 O. Found: 62.7 C, 4.7 H, 23.4 O.

EXAMPLE 6

7-Hydroxy-3,4-dimethylcoumarin 2'-nitrobenzenesulfonate

Yield 23% (ethanol/DMF), mp.: 187°–189° C.
$C_{17}H_{13}NO_7S$ (375) Calculated: 54.4 C, 3.5 H, 3.7 N. Found: 54.5 C, 3.6 H, 3.8 N.

EXAMPLE 7

7-Hydroxy-3,4-dimethylcoumarin 4'-methoxybenzenesulfonate

Yield: 82% (ethanol/DMF), mp.: 138°–140° C.
$C_{18}H_{16}O_6S$ (360) Calculated: 60.0 C, 4.3 H. Found: 60.1 C, 4.5 H.

EXAMPLE 8

7-Hydroxy-3,4-dimethylcoumarin 4'-($\alpha,\alpha,\beta,\beta$-tetrafluoroethoxy)-benzenesulfonate Yield: 78% (ethanol), mp. 123°–126° C.
$C_{19}H_{14}F_4O_6S$ (446) Calculated: 51.1 C, 3.2 H, 7.2 F. Found: 51.2 C, 3.3 H, 7.5 F.

EXAMPLE 9

7-Hydroxy-3,4-dimethylcoumarin 4'-chlorobenzenesulfonate

Yield: 86% (ethanol/DMF), mp.: 170°–172° C.
$C_{17}H_{13}ClO_5S$ (365) Calculated: 56.0 C, 3.6 H, 9.7 Cl. Found: 54.7 C, 3.5 H, 3.7 N.

EXAMPLE 10

7-Hydroxy-3,4-dimethylcoumarin 4'-nitrobenzenesulfonate

Yield: 67% (ethanol/DMF), mp.: 200°–203° C.
$C_{17}H_{13}NO_7S$ (375) Calculated: 54.4 C, 3.5 H, 3.7 N. Found: 54.7 C, 3.5 H, 3.7 N.

EXAMPLE 11

7-Hydroxy-3,4-dimethylcoumarin 4'-bromobenzenesulfonate

Yield: 82% (ethanol/DMF), mp.: 162°–168° C.
$C_{17}H_{13}BrO_5S$ (409) Calculated: 49.9 C, 3.2 H, 19.5 Br. Found: 49.9 C, 3.2 H, 19.3 Br.

EXAMPLE 12

7-Hydroxy-3,4-dimethylcoumarin 2',4',6'-trimethylbenzenesulfonate

Yield: 82% (ethanol/DMF), mp.: 188°–190° C.
$C_{20}H_{20}O_5S$ (372) Calculated: 64.5 C, 5.4 H, 21.5 O. Found: 64.5 C, 5.3 H, 21.6 O.

EXAMPLE 13

7-Hydroxy-3,4-dimethylcoumarin 2',5'-dichlorobenzenesulfonate

Yield: 83% (ethanol/DMF), mp.: 178°–180° C.
$C_{17}H_{12}Cl_2O_5S$ (399) Calculated: 51.1 C, 3.0 H, 17.8 Cl. Found: 51.1 C, 3.0 H, 17.7 Cl.

EXAMPLE 14

7-Hydroxy-3,4-dimethylcoumarin 4'-fluorobenzenesulfonate 5.0 g of 7-hydroxy-3,4-dimethylcoumarin in 20 ml of DMF were added dropwise to a suspension of 1.15 g of 55% strength NaH in 50 ml of DMF at 20° C. After 1 hour, 5.3 g of 4-fluorobenzenesulfonyl chloride were added to the solution, and the mixture was stirred overnight at room temperature and then poured onto 500 g of ice. The precipitate was filtered off under suction, washed with water, dried, and recrystallized from ethanol/DMF.

Yield: 6.7 g (74%), mp.: 162°–165° C.
$C_{17}H_{13}FO_5S$ (348) Calculated: 58.6 C, 3.8 H, 5.5 F. Found: 58.7 C, 3.9 H, 5.4 F.

Using the same method, the following active compounds were prepared:

EXAMPLE 15

7-Hydroxy-3,4-dimethylcoumarin 4'-acetylaminobenzenesulfonate

Yield: 33%, mp.: 194°–195° C.
$C_{19}H_{17}N_6S$ (387) Calculated: 59.9 C, 4.4 H, 24.8 O. Found: 58.8 C, 4.5 H, 24.6 O.

EXAMPLE 16

7-Hydroxy-3,4-dimethylcoumarin 4'-methylthiobenzenesulfonate

Yield: 32%, mp.: 129°–131° C. (ethanol)
$C_{18}H_{16}O_5S_2$ (376) Calculated: 57.4 C, 4.3 H, 21.3 O. Found: 57.8 C, 4.4 H, 21.0 O.

EXAMPLE 17

7-Hydroxy-3,4-dimethylcoumarin 4'-acetylbenzenesulfonate

Yield 49%, mp.: 157°–159° C. (isopropanol/DMF)
$C_{19}H_{16}O_6S$ (372) Calculated: 61.3 C, 4.3 H, 25.8 O. Found: 61.5 C, 4.3 H, 25.7 O.

EXAMPLE 18

7-Hydroxy-3,4-dimethylcoumarin 4'-cyanobenzenesulfonate

Yield: 50%, mp.: 184°–185° C. (ethanol/DMF)
$C_{18}H_{13}NO_5S$ (355) Calculated: 60.8 C, 3.7 H, 3.9 N. Found: 61.1 C, 3.9 H, 3.9 N.

EXAMPLE 19

7-Hydroxy-3-methylcoumarin 4'-bromobenzenesulfonate

Yield: 67%, mp.: 210°–212° C. (ethanol)
$C_{16}H_{11}BrO_5S$ (395) Calculated: 48.6 C, 2.8 H, 20.2 Br. Found: 48.8 C, 3.0 H, 20.0 Br.

EXAMPLE 20

7-Hydroxy-3-methylcoumarin benzenesulfonate

Yield: 68%, mp.: 150°–152° C. (ethanol)

$C_{16}H_{12}O_5S$ (316) Calculated: 60.8 C, 3.8 H. Found: 61.0 C, 3.8 H.

EXAMPLE 21

7-Hydroxy-3,4-tetramethylenecoumarin benzenesulfonate

Yield: 89%, mp.: 185°–186° C. (ethanol/DMF)
$C_{19}H_{16}O_5S$ (356) Calculated: 64.0 C, 4.5 H. Found: 64.1 C, 4.6 H.

EXAMPLE 22

7-Hydroxy-3,4-dimethylcoumarin propanesulfonate

Yield: 64%, mp.: 107° C.
$C_{14}H_{16}O_5S$ (296) Calculated: 56.7 C, 5.4 H. Found: 56.8 C, 5.5 H.

EXAMPLE 23

7-Hydroxy-3,4-dimethylcoumarin isopropanesulfonate

Yield: 58%, mp.: 87° C.
$C_{14}H_{16}O_5S$ (296) Calculated: 56.7 C, 5.4 H. Found: 56.5 C, 5.6 H.

EXAMPLE 24

7-Hydroxy-3,4-dimethylcoumarin trifluoromethanesulfonate

Yield: 31%, mp.: 84° C. (ethanol)
$C_{13}H_9F_3SO_5$ (322) Calculated: 44.7 C, 2.8 H, 17.7 F. Found: 44.8 C, 3.0 H, 16.8 F.

EXAMPLE 25

7-Hydroxy-3,4-dimethylcoumarin phenylmethanesulfonate

Yield: 59%, mp.: 187°–189° C. (ethanol/DMF)
$C_{18}H_{16}O_5S$ (344) Calculated: 62.8 C, 4.7 H. Found: 62.8 C, 4.7 H.

EXAMPLE 26

7-Hydroxy-3,4-dimethylcoumarin butanesulfonate

Yield: 56%, mp.: 101° C.
$C_{15}H_{18}O_5S$ (310) Calculated: 58.1 C, 5.9 H. Found: 57.7 C, 5.8 H.

EXAMPLE 27

7-Hydroxy-3,4-dimethylcoumarin octanesulfonate

Yield: 49%, mp.: 65°–67° C. (ethanol)
$C_{19}H_{26}O_5S$ (366) Calculated: 62.3 C, 7.2 H, 21.8 O. Found: 62.2 C, 7.0 H, 21.9 O.

EXAMPLE 28

7-Hydroxy-3,4-tetramethylenecoumarin 4'-bromobenzenesulfonate

Yield 86%, mp.: 184°–188° C.
$C_{19}H_{15}BrO_5S$ (435) Calculated: 52.4 C, 3.5 H, 18.4 Br. Found: 52.0 C, 3.5 H, 18.1 Br.

EXAMPLE 29

7-Hydroxy-3,4-tetramethylenecoumarin 4'-chlorobenzenesulfonate

Yield: 79%, mp.: 200°–202° C.
$C_{19}H_{15}ClO_5S$ (391) Calculated: 58.4 C, 3.9 H, 9.1 Cl. Found: 58.7 C, 3.9 H, 8.7 Cl.

EXAMPLE 30

7-Hydroxy-3-methylcoumarin 4'-chlorobenzenesulfonate

Yield: 91%, mp.: 190°–193° C.
$C_{16}H_{11}ClO_5S$ (351) Calculated: 54.8 C, 3.2 H, 10.1 Cl. Found: 55.0 C, 3.4 H, 9.9 Cl.

EXAMPLE 31

4-Ethyl-7-hydroxycoumarin 4'-chlorobenzenesulfonate

Yield: 66%, mp.: 155° C. (ethanol/DMF)
$C_{17}H_{13}ClO_5S$ (365) Calculated: 56.0 C, 3.6 H, 21.9 O, 9.7 Cl. Found: 55.9 C, 3.8 H, 21.7 O, 9.8 Cl.

EXAMPLE 32

4-Ethyl-7-hydroxycoumarin benzenesulfonate

Yield: 69%, mp.: 108°–109° C. (methanol)
$C_{17}H_{14}O_5S$ (330) Calculated: 61.8 C, 4.3 H, 24.2 O. Found: 61.9 C, 4.5 H, 24.0 O.

EXAMPLE 33

4-Ethyl-3-methyl-7-hydroxycoumarin benzenesulfonate

Yield: 61%, mp.: 160°–161° C. (ethanol/DMF)
$C_{18}H_{16}O_5S$ (344) Calculated: 62.8 C, 4.7 H, 23.2 O. Found: 62.9 C, 4.8 H, 23.3 O.

EXAMPLE 34

3-Ethyl-7-hydroxy-4-methylcoumarin 4'-chlorobenzenesulfonate

Yield: 58%, mp.: 196°–197° C. (ethanol/DMF)
$C_{18}H_{15}ClO_5S$ (379) Calculated: 57.1 C, 4.0 H, 21.1 O, 9.4 Cl. Found: 57.1 C, 4.0 H, 21.1 O, 9.4 Cl.

EXAMPLE 35

3-Ethyl-7-hydroxy-4-methylcoumarin benzenesulfonate

Yield: 65%, mp.: 147°–148° C.
$C_{18}H_{16}O_5S$ (344) Calculated: 62.8 C, 4.7 H, 23.2 O. Found: 62.8 C, 4.7 H, 23.3 O.

EXAMPLE 36

7-Hydroxy-4-methyl-3-propylcoumarin benzenesulfonate

Yield 63%, mp.: 124°–125° C. (ethanol)
$C_{19}H_{18}O_5S$ (358) Calculated: 63.7 C, 5.1 H, 22.3 O. Found: 64.1 C, 5.1 H, 22.1 O.

EXAMPLE 37

7-Hydroxy-4-methyl-3-propylcoumarin 4'-chlorobenzenesulfonate

Yield: 46%, mp.: 133°–134° C. (ethanol)
$C_{19}H_{17}ClO_5S$ (393) Calculated: 58.1 C, 4.4 H, 20.4 O, 9.0 Cl. Found: 58.4 C, 4.5 H, 20.1 O, 8.9 Cl.

EXAMPLE 38

7-Hydroxy-3,4-dimethylcoumarin pentanesulfonate

Yield 44%, mp.: 72°–74° C. (ethanol)
$C_{16}H_{20}O_5S$ (324) Calculated: 59.2 C, 6.2 H, 24.7 O. Found: 58.7 C, 6.2 H, 24.4 O.

EXAMPLE 39

7-Hydroxy-3,4-dimethylcoumarin ethanesulfonate 5.0 g of 7-hydroxy-3,4-dimethylcoumarin were dissolved in 20 ml of $H_2O$/1.1 g of NaOH at room temperature, while stirring, and 3.4 g of ethanesulfonyl chloride were added. The mixture was stirred overnight, and the precipitate was filtered off under suction and recrystallized from ethanol.

Yield: 6.2 g (84%), mp.: 117°–118° C.
$C_{13}H_{14}O_5S$ (282) Calculated: 55.3 C, 5.0 H, 28.3 O. Found: 55.1 C, 5.0 H, 28.5 O.

EXAMPLE 40

7-Hydroxy-4-methylcoumarin 4'-chlorobenzenesulfonate

Yield: 53%, mp.: 163° C. (ethanol)
$C_{16}H_{11}ClO_5S$ (351) Calculated: 54.8 C, 3.2 H, 10.1 Cl. Found: 54.9 C, 3.4 H, 10.1 Cl.

EXAMPLE 41

7-Hydroxy-4-methylcoumarin benzenesulfonate

Yield 81%, mp.: 87° C. (ethanol)
$C_{16}H_{12}O_5S$ (316) Calculated: 60.8 C, 3.8 H, 25.3 O. Found: 61.1 C, 4.0 H, 25.3 O.

EXAMPLE 42

7-Hydroxy-4-methylcoumarin methanesulfonate

Yield: 49%, mp.: 164° C. (ethanol)
$C_{11}H_{10}O_5S$ (254) Calculated: 52.0 C, 4.0 H, 31.5 O. Found: 52.0 C, 4.0 H, 31.8 O.

EXAMPLE 43

7-Hydroxy-3,4-dimethylcoumarin N-methylamidosulfonate

Yield: 26%, mp.: 146° C. (ethanol)
$C_{12}H_{13}NO_5S$ (283) Calculated: 50.9 C, 4.6 H, 4.9 N. Found: 51.0 C, 4.7 H, 4.9 N.

EXAMPLE 44

7-Hydroxycoumarin methanesulfonate

Yield: 54%, mp.: 144° C. (ethanol)
$C_{10}H_8O_5S$ (240) Calculated: 50.0 C, 3.3 H, 33.5 O. Found: 50.5 C, 3.7 H, 33.3 O.

EXAMPLE 45

7-Hydroxycoumarin isopropanesulfonate

Yield: 40%, mp.: 110° C. (ethanol)
$C_{12}H_{12}O_5S$ (268) Calculated: 53.7 C, 4.5 H, 29.8 O. Found: 53.9 C, 4.6 H, 29.7 O.

EXAMPLE 46

7-Hydroxy-3,4-dimethylcoumarin 4'-methanesulfonylbenzenesulfonate 4.0 g of 7-hydroxy-3,4-dimethylcoumarin 4'-methylthiobenzenesulfonate were dissolved in 160 ml of $CH_2Cl_2$/20 ml of $CH_3OH$, and a solution of 4.7 g of 85% strength 3-chloroperbenzoic acid in 50 ml of $CH_2Cl_2$ was added at room temperature. The solution was stirred overnight, the solvent was stripped off, the residue was dissolved in $CH_2Cl_2$, the solution was washed several times with $NaHCO_3$ solution and dried over $Na_2SO_4$, the solvent was distilled off and the residue was then recrystallized from ethanol/DMF.

Yield: 1.7 g (38%), mp.: 227°–228° C.
$C_{18}H_{16}O_7S_2$ (408) Calculated: 52.9 C, 4.0 H, 27.1 O. Found: 53.0 C, 3.9 H, 27.4 O.

EXAMPLE 47

7-Hydroxy-3-carbomethoxymethyl-4-methylcoumarin benzenesulfonate

Yield: 36%, mp.: 95°–97° C.
$C_{18}H_{14}O_7S$ (374) Calculated: 57.8 C, 3.8 H. Found: 57.5 C, 4.0 H.

EXAMPLE 48

7-Hydroxy-3-carbomethoxymethyl-4-methylcoumarin 4'-bromobenzenesulfonate

Yield: 35%, mp.: 176°–177° C. (ethanol/DMF)
$C_{18}H_{13}BrO_7S$ (453) Calculated: 47.7 C, 2.9 H, 17.6 Br. Found: 47.9 C, 3.2 H, 17.0 Br.

EXAMPLE 49

7-Hydroxy-3-carboethoxycoumarin benzenesulfonate

Yield: 63%, mp.: 134°–135° C. (ethanol)
$C_{18}H_{13}O_7S$ (374) Calculated: 57.8 C, 3.8 H, 29.9 O. Found: 57.8 C, 3.6 H, 29.8 O.

EXAMPLE 50

7-Hydroxy-3-carboethoxycoumarin 4'-chlorobenzenesulfonate

Yield: 72%, mp.: 168°–169° C. (ethanol/DMF)
$C_{18}H_{13}ClO_7S$ (409) Calculated: 52.9 C, 3.2 H, 27.4 O, 8.7 Cl. Found: 52.9 C, 3.3 H, 27.2 O, 8.6 Cl.

EXAMPLE 51

7-Hydroxy-3-carboethoxycoumarin 4'-nitrobenzenesulfonate

Yield: 22%, mp.: 185°–187° C. (ethanol/DMF)
$C_{18}H_{13}NO_9S$ (419) Calculated: 51.6 C, 3.1 H, 3.3 N. Found: 51.8 C, 3.2 H, 3.5 N.

EXAMPLE 52

7-Hydroxy-3,4-dimethylcoumarin 2'-methylpropanesulfonate

Yield: 65%, mp.: 120° C. (ethanol)
$C_{15}H_{18}O_5S$ (310) Calculated: 58.1 C, 5.9 H, 25.8 O. Found: 58.5 C, 5.8 H, 25.8 O.

EXAMPLE 53

6-Hydroxy-3,4-dimethylcoumarin benzenesulfonate

Yield: 40%, mp.: 147°–150° C.
$C_{17}H_{14}O_5S$ (330) Calculated: 61.8 C, 4.3 H, 24.2 O. Found: 62.1 C, 4.2 H, 24.0 O.

EXAMPLE 54

7-Hydroxycoumarin benzenesulfonate

Yield: 46%, mp.: 132°–135° C. (ethanol)
$C_{15}H_{10}O_5S$ (302) Calculated: 59.6 C, 3.3 H, 26.4 O. Found: 59.6 C, 3.5 H, 26.7 O.

EXAMPLE 55

7-Hydroxy-3,4-dimethylcoumarin 3'-chloropropanesulfonate

Yield: 75%, mp.: 96°–98° C. (i-propanol)
$C_{14}H_{15}ClO_5S$ (331) Calculated: 50.8 C, 4.6 H, 24.2 O, 10.7 Cl. Found: 51.1 C, 4.6 H, 24.4 O, 10.2 Cl.

EXAMPLE 56

7-Hydroxy-3,4-dimethylcoumarin chloromethanesulfonate

Yield: 34%, mp.: 142°–144° C. (ethanol)
$C_{12}H_{11}ClO_5S$ (302) Calculated: 48.2 C, 3.8 H, 11.4 Cl.
Found: 47.7 C, 3.6 H, 11.8 Cl.

EXAMPLE 57

7-Hydroxy-3,4-dimethylcoumarin 3'-nitrobenzenesulfonate

Yield: 30%, mp.: 172°–175° C. (ethanol)
$C_{17}H_{17}NO_7S$ (375) Calculated: 54.4 C, 3.5 H, 3.7 N.
Found: 54.7 C, 3.6 H, 3.8 N.

EXAMPLE 58

7-Hydroxy-3,4-dimethylcoumarin 4'-trifluoromethylthiobenzenesulfonate

Yield: 65%, mp.: 95°–96° C. (i-propanol)
$C_{18}H_{13}F_3O_5S_2$ (430) Calculated: 50.2 C, 3.0 H, 13.2 F.
Found: 50.5 C, 3.3 H, 13.2 F.

EXAMPLE 59

7-Hydroxy-3-chloro-4-methylcoumarin benzenesulfonate

Yield: 44%, mp.: 143°–146° C. (i-propanol)
$C_{16}H_{11}ClO_5S$ (351) Calculated: 54.8 C, 3.2 H, 22.8 O, 10.1 Cl. Found: 55.1 C, 3.2 H, 22.8 O, 10.1 Cl.

EXAMPLE 60

7-Hydroxy-3-chloro-4-methylcoumarin isopropanesulfonate

Yield 23%, mp.: 89°–90° C. (i-propanol)
$C_{13}H_{13}ClO_5S$ (317) Calculated: 49.3 C, 4.1 H, 25.3 O, 11.2 Cl. Found: 49.1 C, 4.0 H, 25.2 O, 11.7 Cl.

EXAMPLE 61

7-Hydroxy-3,4-dimethylcoumarin 4'-trifluoromethylsulfonylbenzenesulfonate 16 g of the substance from Example 58 were oxidized as described in Example 46.
Yield: 9.1 g (53%), mp.: 170°–173° C. (ethyl acetate)
$C_{18}H_{13}F_3O_7S_2$ (462) Calculated: 46.8 C, 2.8 H, 12.3 F.
Found: 46.7 C, 3.0 H, 11.8 F.

We claim:

1. A hydroxycoumarin sulfonate of formula I

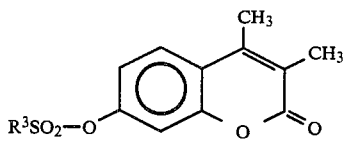

wherein $R^3$ is a straight-chain or branched alkyl radical of 1 to 8 carbon atoms which can be substituted by halogen, or $R^3$ is an amino group —$NR^4R^5$ or phenyl or naphthyl, each aryl of which is unsubstituted or mono-, di- or tri-substituted by —$NO_2$, halogen, —CN, or a combination of these substituents, wherein $R^4$ and $R^5$ are identical or different and each is hydrogen or alkyl of 1 to 4 carbon atoms.

2. A compound according to claim 1 wherein $R^3$ is alkyl of 2 to 4 carbon atoms, fluoroalkyl of 1 to 2 carbon atoms or a phenyl radical which is unsubstituted or substituted according to claim 1.

3. A composition for the oral or intravenous treatment of depression which contains, as the active compound, an effective amount of a compound as claimed in claim 2 together with a pharmaceutical carrier therefor.

4. A composition for the oral or intravenous treatment of depression and allergic disorders which contains, as the active compound, an effective amount of a compound as claimed in claim 1 together with a pharmaceutical carrier therefor.

5. A method of treating depression which comprises orally administering to the patient an effective amount of a composition according to claim 4.

6. A method of treating depression which comprises intravenously administering to the patient an effective amount of a composition according to claim 4.

7. A method of treating depression which comprises orally administering to the patient a pharmaceutical composition containing an effective amount of at least one compound of the formula I

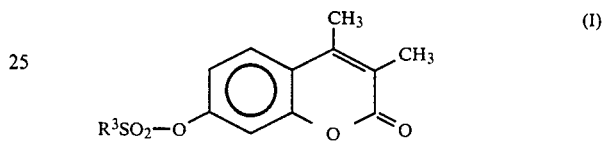

wherein $R^3$ is a straight-chain or branched alkyl radical of 1 to 8 carbon atoms or cycloalkyl of 3 to 8 carbon atoms, each of which can be substituted by halogen, —$OR^4$, —$NR^4R^5$, —CN or phenyl, or $R^3$ is a straight chain or branched alkenyl radical of 3 to 8 carbon atoms, an amino group —$NR^4R^5$ or phenyl or naphthyl, each aryl of which is unsubstituted or mono-, di- or tri-substituted by —$OR^4$, —$NR^4R^5$, —$NO_2$, halogen, —$SR^4$, —$S(O)R^4$, —$S(O_2)R^4$, —$SCF_3$, —$S(O_2)CF_3$, —CN, —$C(O)R^4$, —$OC(O)R^4$, —$NCH(O)R^4$, —$CF_3$, $C_1$-$C_4$-alkyl or a combination of these substituents, wherein $R^4$ and $R^5$ are identical or different and each is hydrogen or alkyl of 1 to 4 carbon atoms.

8. A method of treating depression which comprises intravenously administering to the patient a pharmaceutical composition containing an effective amount of at least one compound of the formula I

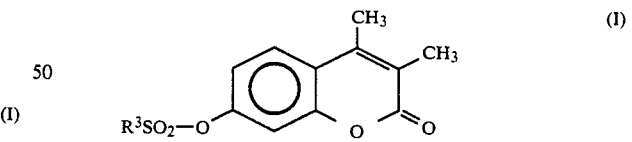

wherein $R^3$ is a straight-chain or branched alkyl radical of 1 to 8 carbon atoms or cycloalkyl of 3 to 8 carbon atoms, each of which can be substituted by halogen, —$OR^4$, —$NR^4R^5$, —CN or phenyl, or $R^3$ is a straight chain or branched alkenyl radical of 3 to 8 carbon atoms, an amino group —$NR^4R^5$ or phenyl or naphthyl, each aryl of which is unsubstituted or mono-, di- or tri-substituted by —$OR^4$, —$NR^4R^5$, —$NO_2$, halogen, —$SR^4$, —$S(O)R^4$, —$S(O_2)R^4$, —$SCF_3$, —$S(O_2)CF_3$, —CN, —$C(O)R^4$, —$OC(O)R^4$, —$NCH(O)R^4$, —$CF_3$, $C_1$-$C_4$-alkyl or a combination of these substituents, wherein $R^4$ and $R^5$ are identical or different and each is hydrogen or alkyl of 1 to 4 carbon atoms.

* * * * *

UNITED STATES PATENT AND TRADEMARK OFFICE
CERTIFICATE OF CORRECTION

PATENT NO. : 4,618,622

DATED : October 21, 1986

INVENTOR(S) : T.E. Nowlin

It is certified that error appears in the above-identified patent and that said Letters Patent is hereby corrected as shown below:

Col. 11, line 33, "unecessary" should be --unnecessary--.
Col. 25, line 14, "Condtions" shoulde be --conditions --.
Col. 26, Claim 1, line 8, before "halogen" insert --a--.
Col. 27, Claim 17, line 12, before "$C_1-C_4$" insert --a--.
Col. 27, Claim 21, line 35, before "halogen" insert --a--.
Col. 28, Claim 27, line 18, "moles" should be --mmoles--.
Col. 28, Claim 29, line 25, before "halogen" insert --a--.
Col. 28, Claim 39, line 1, change "process" to --catalyst composition--.
Col. 28, Claim 41, line 57, "alphaolefin" should be --alpha olefin--.
Col. 28, Claim 41, line 58, before "polymer" insert --the--.
Col. 31, Claim 70, line 34, before "of" insert --titanium--.
Col. 32, Claim 88, line 44, "isoproxide" should be --isopropoxide--.

Signed and Sealed this

Twenty-second Day of May, 1990

Attest:

HARRY F. MANBECK, JR.

Attesting Officer

Commissioner of Patents and Trademarks